United States Patent [19]

Tumer

[11] Patent Number: 4,970,168
[45] Date of Patent: Nov. 13, 1990

[54] VIRUS-RESISTANT PLANTS

[75] Inventor: Nilgun E. Tumer, Chesterfield, Mo.

[73] Assignee: Monsanto Company, St. Louis, Mo.

[21] Appl. No.: 302,498

[22] Filed: Jan. 27, 1989

[51] Int. Cl.⁵ .......................... C12N 1/00; C12N 1/20; C12N 5/00; C12N 15/00

[52] U.S. Cl. .............................. 435/317.1; 435/172.3; 435/240.4; 435/252.3; 435/252.33; 435/320; 435/71.1; 800/205; 800/DIG. 42

[58] Field of Search .................. 435/240.4, 320, 317.1, 435/252.3, 252.33, 172.3; 800/1, 205, DIG. 42

[56] References Cited

PUBLICATIONS

Abel et al., 1986, Science 232:738–743.
Morozou et al., 1983, Dokladi Academi Nauk SSSR, 271:211–215.
Shukla et al., 1986, Virology 152:118–125.
Rosner et al., 1986, Plant Pathology 35:178–184.
Ooms et al., 1987, Theor Appl Genet 73:744–750.
Hemenway et al., 1988 (May) Embo J. 7:1273–1280.
Beachy et al., 1987, Genetic Engineering of Plants for Protection Against Virus Diseases in Plant Resistance to Viruses; Wiley; pp. 151–169.

*Primary Examiner*—Charles F. Warren
*Assistant Examiner*—P. Rhodes
*Attorney, Agent, or Firm*—Dennis R. Hoerner, Jr.; Thomas P. McBride; James C. Bolding

[57] ABSTRACT

Transgenic plants are disclosed which are resistant to virus infection by Potato Virus X and Potato Virus Y. Plant genes and transformation vectors are also disclosed. Potato plants, for example, Russet Burbank variety, are made resistant to dual infection by Potato Virus X and Potato Virus Y by transforming the plant to express the coat proteins of the two viruses.

7 Claims, 6 Drawing Sheets

```
      GCAAATGACACAATTGATGCAGGAGGAAGCAACAAGAAAGATACAAAACCAGAGCAAAGC
  1   ---------+---------+---------+---------+---------+---------+  60
      CGTTTACTGTGTTAACTACGTCCTCCTTCGTTGTTCTTTCTATGTTTTGGTCTCGTTTCG

A  N  D  T  I  D  A  G  G  S  N  K  K  D  T  K  P  E  Q  S  -

AGCATCCAGTCAAACCCGAACAAAGGAAAAGATAAAGATGTCAATGCCGGCACATCTGGG
  61  ---------+---------+---------+---------+---------+---------+  120
      TCGTAGGTCAGTTTGGGCTTGTTTCCTTTTCTATTTCTACACTTACGGCCGTGTAGACCC

S  I  Q  S  N  P  N  K  G  K  D  K  D  V  N  A  G  T  S  G  -

ACACATACTGTGCCGAGAATCAAGGCTATCACGTCCAAAATGAGAATGCCCAAAAGCAAG
 121  ---------+---------+---------+---------+---------+---------+  180
      TGTGTATGACACGGCTCTTAGTTCCGATAGTGCAGGTTTTACTCTTACGGGTTTTCGTTC

T  H  T  V  P  R  I  K  A  I  T  S  K  M  R  M  P  K  S  K  -

GGAGCAGCCGTGCTAAATTTAGAACACTTGCTTGAGTATGCTCCACAACAAATTGATATT
 181  ---------+---------+---------+---------+---------+---------+  240
      CCTCGTCGGCACGATTTAAATCTTGTGAACGAACTCATACGAGGTGTTGTTTAACTATAA

G  A  A  V  L  N  L  E  H  L  L  E  Y  A  P  Q  Q  I  D  I  -

TCAAATACTCGGGCAACTCAATCACAGTTTGATACGTGGTATGAGGCAGTGCGGATGGCA
 241  ---------+---------+---------+---------+---------+---------+  300
      AGTTTATGAGCCCGTTGAGTTAGTGTCAAACTATGCACCATACTCCGTCACGCCTACCGT

S  N  T  R  A  T  Q  S  Q  F  D  T  W  Y  E  A  V  R  M  A  -

TACGACATAGGAGAAACTGAGATGCCAACTGTGATGAATGGGCTTATGGTTTGGTGCATT
 301  ---------+---------+---------+---------+---------+---------+  360
      ATGCTGTATCCTCTTTGACTCTACGGTTGACACTACTTACCCGAATACCAAACCACGTAA

Y  D  I  G  E  T  E  M  P  T  V  M  N  G  L  M  V  W  C  I  -

GAAAATGGAACCTCGCCAAATGTCAACGGAGTTTGGGTTATGATGGATGGGAATGAACAA
 361  ---------+---------+---------+---------+---------+---------+  420
      CTTTTACCTTGGAGCGGTTTACAGTTGCCTCAAACCCAATACTACCTACCCTTACTTGTT

E  N  G  T  S  P  N  V  N  G  V  W  V  M  M  D  G  N  E  Q  -

GTTGAGTACCCGTTGAAACCAATCGTTGAGAATGCAAAACCAACCCTTAGGCAAATCATG
 421  ---------+---------+---------+---------+---------+---------+  480
      CAACTCATGGGCAACTTTGGTTAGCAACTCTTACGTTTTGGTTGGGAATCCGTTTAGTAC

V  E  Y  P  L  K  P  I  V  E  N  A  K  P  T  L  R  Q  I  M  -

GCACATTTCTCAGATGTTGCAGAAGCGTATATAGAAATGCGCAACAAAAAGGAACCATAT
 481  ---------+---------+---------+---------+---------+---------+  540
      CGTGTAAAGAGTCTACAACGTCTTCGCATATATCTTTACGCGTTGTTTTCCTTGGTATA

```
     ATGCCACGATATGGTTTAGTTCGAAATCTGCGGGATGTGGGTTTAGCGCGTTATGCTTTT
541  ---------+---------+---------+---------+---------+---------+ 600
     TACGGTGCTATACCAAATCAAGCTTTAGACGCCCTACACCCAAATCGCGCAATACGAAAA

M  P  R  Y  G  L  V  R  N  L  R  D  V  G  L  A  R  Y  A  F  -

GACTTTTATGAGGTCACATCACGAACACCAGTGAGGGCTAGGGAAGCGCACATTCAAATG
601  ---------+---------+---------+---------+---------+---------+ 660
     CTGAAAATACTCCAGTGTAGTGCTTGTGGTCACTCCCGATCCCTTCGCGTGTAAGTTTAC

D  F  Y  E  V  T  S  R  T  P  V  R  A  R  E  A  H  I  Q  M  -

AAGGCCGCAGCATTGAAATCAGCCCAACCTCGACTTTTCGGGTTGGACGGTGGCATCAGT
661  ---------+---------+---------+---------+---------+---------+ 720
     TTCCGGCGTCGTAACTTTAGTCGGGTTGGAGCTGAAAAGCCCAACCTGCCACCGTAGTCA

K  A  A  L  K  S  A  Q  P  R  L  F  G  L  D  G  G  I  S  -

ACACAAGAGGAGAACACAGAGAGGCACAGGACCGAGGATGTCTCTCCAAGTATGCATACT
721  ---------+---------+---------+---------+---------+---------+ 780
     TGTGTTCTCCTCTTGTGTCTCTCCGTGTCCTGGCTCCTACAGAGAGGTTCATACGTATGA

T  Q  E  E  N  T  E  R  H  R  T  E  D  V  S  P  S  M  H  T  -

CTACTTGGAGTCAAGAACATG
781  ---------+---------+- 801
     GATGAACCTCAGTTCTTGTAC

```
     ATGTCAGCACCAGCTAGCACAACACAGGCCACAGGGTCAACTACCTCAACTACCACAAAA
  1  ---------+---------+---------+---------+---------+---------+  60
     TACAGTCGTGGTCGATCGTGTTGTGTCCGGTGTCCCAGTTGATGGAGTTGATGGTGTTTT

M  S  A  P  A  S  T  T  Q  A  T  G  S  T  T  S  T  T  T  K   -

ACTGCAGGCGCAACTCCTGCCACAGCTTCAGGACTGTTCACCATCCCGGATGGGGATTTC
 61  ---------+---------+---------+---------+---------+---------+  120
     TGACGTCCGCGTTGAGGACGGTGTCGAAGTCCTGACAAGTGGTAGGGCCTACCCCTAAAG

T  A  G  A  T  P  A  T  A  S  G  L  F  T  I  P  D  G  D  F   -

TTTAGTACAGCCCGTGCTGTAATAGCCAGCAATGCCGTTGCAACAAATGAGGACCTCAGC
121  ---------+---------+---------+---------+---------+---------+  180
     AAATCATGTCGGGCACGACATTATCGGTCGTTACGGCAACGTTGTTTACTCCTGGAGTCG

F  S  T  A  R  A  V  I  A  S  N  A  V  A  T  N  E  D  L  S   -

AAGATTGAGGCTATCTGGAAGGACATGAAGGTGCCCACAGACACTATGGCACAGGCTGCT
181  ---------+---------+---------+---------+---------+---------+  240
     TTCTAACTCCGATAGACCTTCCTGTACTTCCACGGGTGTCTGTGATACCGTGTCCGACGA

K  I  E  A  I  W  K  D  M  K  V  P  T  D  T  M  A  Q  A  A   -

TGGGACTTAGTCAGACACTGTGCTGATGTGGGCTCATCTGCTCAAACAGAAATGATAGAT
241  ---------+---------+---------+---------+---------+---------+  300
     ACCCTGAATCAGTCTGTGACACGACTACACCCGAGTAGACGAGTTTGTCTTTACTATCTA

W  D  L  V  R  H  C  A  D  V  G  S  S  A  Q  T  E  M  I  D   -

ACGGGTCCCTATTCCAACGGCATCAGCAGAGCCAGACTGGCAGCAGCAATCAAAGAGGTG
301  ---------+---------+---------+---------+---------+---------+  360
     TGCCCAGGGATAAGGTTGCCGTAGTCGTCTCGGTCTGACCGTCGTCGTTAGTTTCTCCAC

T  G  P  Y  S  N  G  I  S  R  A  R  L  A  A  A  I  K  E  V   -

TGCACACTTAGGCAATTTTGCATGAAGTATGCCCCAGTGGTATGGAACTGGATGCTGACT
361  ---------+---------+---------+---------+---------+---------+  420
     ACGTGTGAATCCGTTAAAACGTACTTCATACGGGGTCACCATACCTTGACCTACGACTGA

C  T  L  R  Q  F  C  M  K  Y  A  P  V  V  W  N  W  M  L  T   -

AACAACAGTCCGCCTGCTAACTGGCAAGCGCAAGGTTTCAAGCCTGAGCACAAATTCGCT
421  ---------+---------+---------+---------+---------+---------+  480
     TTGTTGTCAGGCGGACGATTGACCGTTCGCGTTCCAAAGTTCGGACTCGTGTTTAAGCGA

N  N  S  P  P  A  N  W  Q  A  Q  G  F  K  P  E  H  K  F  A   -

GCATTCGACTTCTTCAATGGAGTCACCAACCCAGCTGCCATCATGCCCAAAGAGGGGCTC
481  ---------+---------+---------+---------+---------+---------+  540
     CGTAAGCTGAAGAAGTTACCTCAGTGGTTGGGTCGACGGTAGTACGGGTTTCTCCCCGAG

```
        ATTCGGCCACCGTCTGAAGCTGAAATGAATGCTGCCCAAACTGCTGCCTTTGTGAAGATT
    541 ---------+---------+---------+---------+---------+---------+ 600
        TAAGCCGGTGGCAGACTTCGACTTTACTTACGACGGGTTTGACGACGGAAACACTTCTAA

I  R  P  P  S  E  A  E  M  N  A  A  Q  T  A  A  F  V  K  I  -

ACAAAGGCCAGGGCACAATCCAACGACTTTGCCAGCCTAGACGCAGCTGTCACTCGAGGT
    601 ---------+---------+---------+---------+---------+---------+ 660
        TGTTTCCGGTCCCGTGTTAGGTTGCTGAAACGGTCGGATCTGCGTCGACAGTGAGCTCCA

T  K  A  R  A  Q  S  N  D  F  A  S  L  D  A  A  V  T  R  G  -

CGTATCACTGGAACAACAACCGCTGAGGCTGTTGTCACTCTACCACCACCA
    661 ---------+---------+---------+---------+---------+- 711
        GCATAGTGACCTTGTTGTTGGCGACTCCGACAACAGTGAGATGGTGGTGGT

VIRUS-RESISTANT PLANTS

BACKGROUND OF THE INVENTION

Potato plants are infected by many viruses of economic importance. Potato field surveys often find plants infected with more than one virus that exhibit disease symptoms which are more severe than plants infected with only one virus. Potato Virus X (PVX) is present in many potato fields generally causing mild symptoms and has been referred to as the "healthy potato virus." The presence of mild strains of PVX may protect potato plants from infection with severe PVX strains.

Plants doubly infected with PVX and Potato Virus Y (PVY) may produce severe disease symptoms with high PVX titers (Rochow and Ross, 1974). PVX titers have been shown to increase as much as ten fold in the presence of PVY, with mild strains of PVX increasing more than severe strains. Apparently, the increase in PVX titers in dual viral infections is due to increased synthesis of PVX per cell as opposed to an increase in the number of infected cells (Goodman and Ross, 1974). Tobacco Mosaic Virus (TMV) and/or Cucumber Mosaic Virus (CMV) dual infection with PVX in tobacco plants showed a synergistic increase of disease symptoms but only TMV/PVX and PVY/PVX infections resulted in increased PVX titers (Close, 1964). PVX must be present in the plant before inoculation with TMV or PVY to exhibit the synergistic activity. The PVX/PVY synergism does not occur in plants systemically infected first with PVY (Rochow and Ross, 1974). It has been suggested that the PVX/PVY synergism is caused by PVY interfering with a factor produced by PVX which limits PVX replication (Damirdagh and Ross, 1967).

Genetically engineered resistance to virus infection by expression of viral coat protein in plants has been demonstrated for Tobacco Mosaic Virus (Powell-Abel, et al., 1986), Alfalfa Mosaic Virus (Tumer, et al., 1987), Cucumber Mosaic Virus (Cuozzo, et al., 1988), Potato Virus X (Hemenway, et al., 1988), and Tobacco Streak Virus (van Dun, et al., 1988). However, the pronounced synergistic effect of PVX/PVY infections in plants such as tobacco and more particularly potato renders it unpredictable whether the coat protein expression route would be efficacious in this situation.

BRIEF DESCRIPTION OF THE DRAWINGS

FIG. 1 represents the nucleotide sequence of a coat protein gene of PVY and its deduced amino acid sequence.

FIG. 3 represents the nucleotide sequence of a coat protein gene of PVX and its deduced amino acid sequence.

STATEMENT OF THE INVENTION

Figure 2:
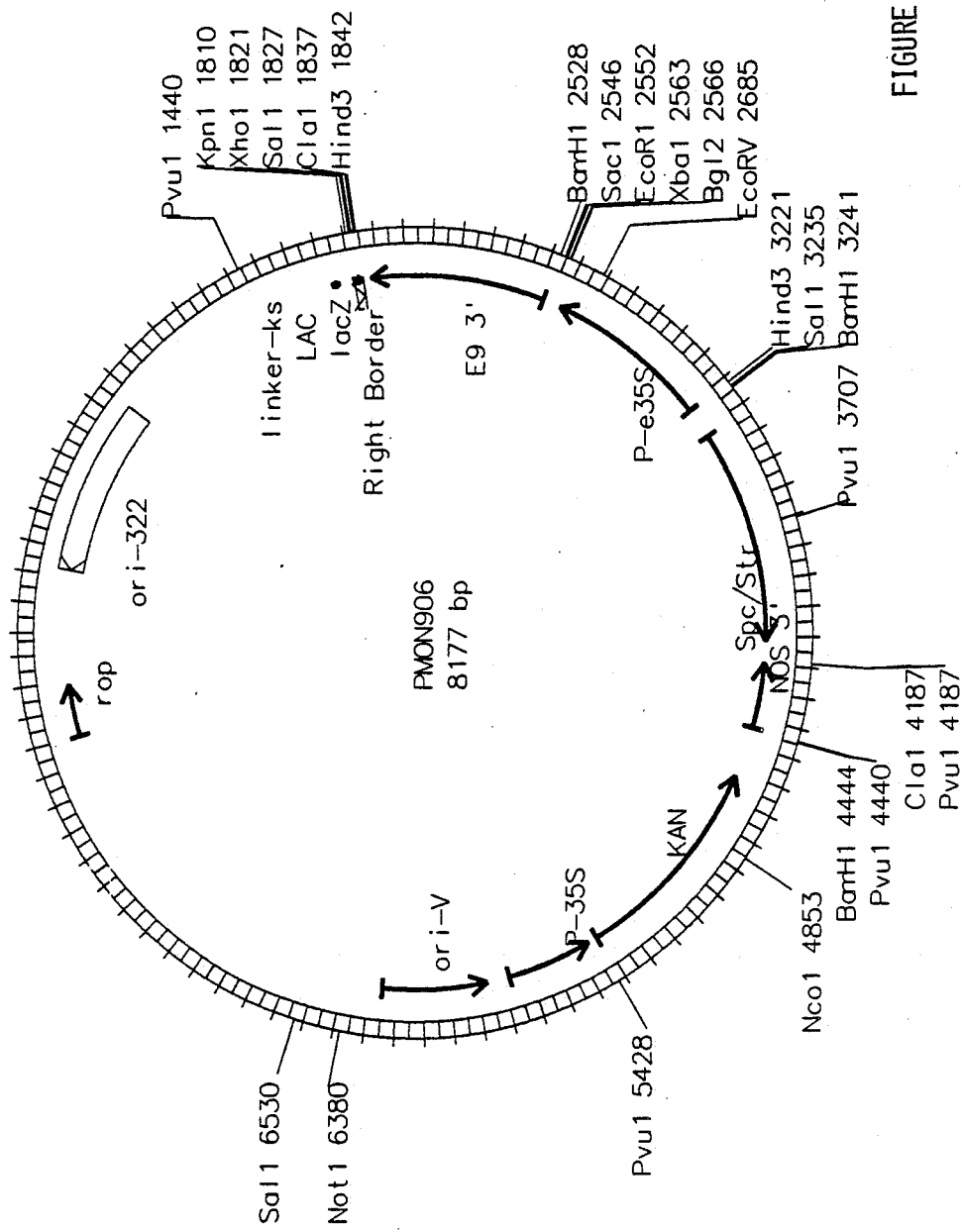
FIG. 2 illustrates a plasmid map of intermediate plant transformation vector pMON906.
Figure 4:
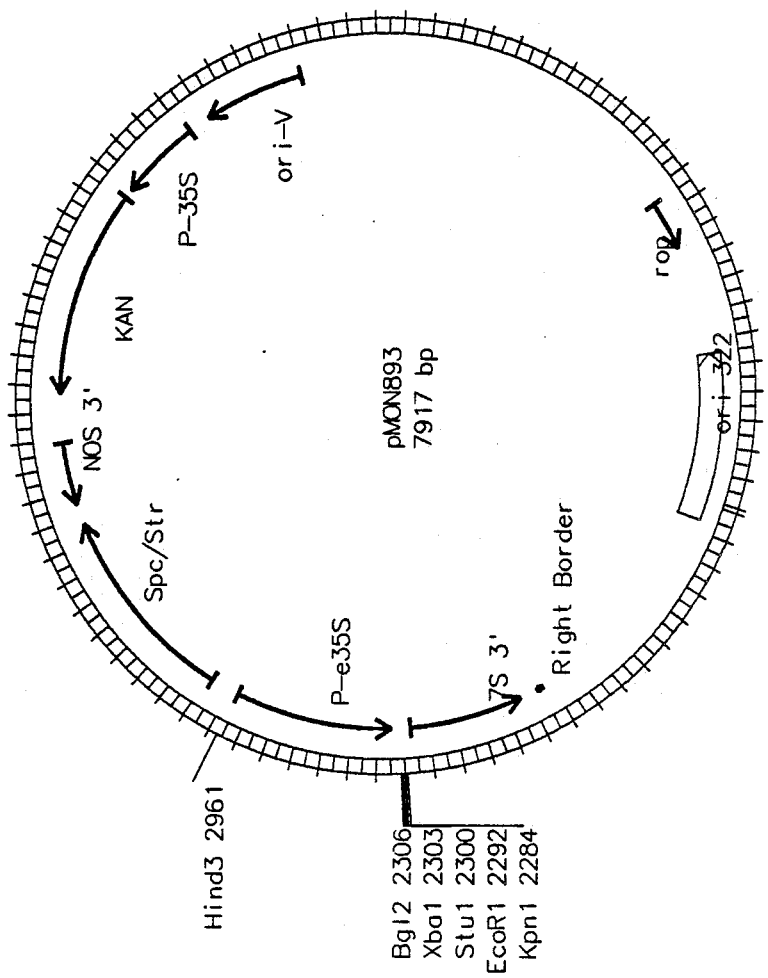
FIG. 4 illustrates a plasmid map of intermediate plant transformation vector pMON893.

The present invention relates to genetically engineered plants and more particularly to such plants which are resistant to PVX and PVY. Plants which can be made resistant to PVX and PVY include, but are not limited to, potato and tobacco. Potato is of particular interest inasmuch as it is the primary target for PVX and PVY.

Accordingly, the present invention provides a method for genetically engineering plants by insertion into the plant genome a DNA construct containing, inter alia, a small portion of the viral genome of PVX and PVY such that the engineered plants display resistance to the plant virus.

In accomplishing the foregoing results, there has been provided, in accordance with one aspect of the present invention, a method of producing genetically transformed plants which are resistant to infection by plant viruses PVX and PVY which comprises inserting into the genome of the plant a DNA sequence which causes the production of the viral coat proteins of PVX and PVY.

In accordance with another aspect of the present invention there is provided a DNA sequence which functions in plant cells to cause the production of the coat proteins of PVX and PVY. There has also been provided, in accordance with yet another aspect of the present invention, bacterial and transformed plant cells that contain the above described DNA. In accordance with yet another aspect of the present invention, a differentiated potato plant has been provided that comprises transformed potato cells which express the coat protein of PVX and PVY and which plant exhibits resistance to infection by PVX and PVY.

Other features and advantages of the present invention will become apparent from the following description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the viral RNA. Transcription of DNA into mRNA is regulated by a region of DNA usually referred to as the "promoter." The promoter region contains a sequence of bases that signals RNA polymerase to associate with the DNA, and to initiate the transcription of mRNA using one of the DNA strands as a template to make a corresponding strand of RNA.

A number of promoters which are active in plant cells have been described in the literature. These include the nopaline synthase (NOS) and octopine synthase (OCS) promoters (which are carried on tumor-inducing plasmids of *Agrobacterium tumefaciens*), the Cauliflower Mosaic Virus (CaMV) 19S and 35S promoters and the light-inducible promoter from the small subunit of ribulose bis-phosphate carboxylase (ssRUBISCO, a very abundant plant polypeptide). All of these promoters and others have been used to create various types of DNA constructs which have been expressed in plants.

Promoters which are known or are found to cause transcription of viral RNA in plant cells can be used in the present invention. Such promoters may be obtained from plants or viruses and include, but are not limited to, the CaMV35S promoter and promoters isolated from plant genes such as ssRUBISCO genes. As described below, it is preferred that the particular promoter selected should be capable of causing sufficient expression to result in the production of an effective amount of coat protein to render the plant substantially resistant to virus infection. The amount of coat protein needed to induce resistance may vary with the type of plant. Accordingly, while the CaMV35S promoter is preferred, it should be understood that this promoter may not be the optimal one for all embodiments of the present invention.

The promoters used in the DNA constructs of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis as well as tandem or multiple copies of enhancer elements, etc.

The DNA constructs of the present invention contain, in double-stranded DNA form, a portion of the virus genome that encodes the coat protein of PVX and PVY. In the case of potyviruses, such as PVY, the coat protein is part of a polyprotein which is processed to release the coat protein. Those skilled in the art should take &his into account to isolate the region of the virus genome that encodes the coat protein and to introduce appropriate translation initiation signals when constructing the plant genes.

A coding sequence used in a DNA construct of this invention may be modified, if desired, to create mutants, either by random or controlled mutagenesis, using methods known to those skilled in the art. Such mutants and variants are therefore within the scope of the present invention. Accordingly, the phrase "coat protein" is used here to include truncated proteins and fusion proteins, as well as unmodified coat protein.

The 3' non-translated region contains a polyadenylation signal which functions in plants to cause the addition of polyadenylate nucleotides to the 3' end of the viral RNA. Examples of suitable 3' regions are (1) the 3' transcribed, non-translated regions containing the polyadenylation signal of the tumor-inducing (Ti) plasmid genes of Agrobacterium, such as the nopaline synthase (NOS) gene, and (2) plant genes like the 7s soybean storage protein genes and the pea E9 small subunit of the RuBP carboxylase gene. An example of a preferred 3' region is that from the E9 gene, described in greater detail in the examples below.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNA's, from suitable eukaryotic genes, or from a synthetic gene sequence. The present invention is not limited to constructs, as presented in the following examples, wherein the non-translated region is derived from the 5' non-translated sequence that accompanies the promoter sequence. Rather, the non-translated leader sequence can be part of the 5' end of the non-translated region of the native coding sequence for the virus coat protein, or part of the promoter sequence, or can be derived from an unrelated promoter or coding sequence as discussed above.

While in most cases the DNA which is inserted into plant cells will contain separate genes which encode individually for PVX and PVY coat proteins, such is not critical. In such cases, each gene would contain a 5' promoter region, a 5' non-translated region, a structural coding region which encodes either PVY or PVX coat protein as well as a 3' non-translated region containing a functional polyadenylation signal. Those skilled in the art will recognize that one may be able to produce a fusion polypeptide containing PVX and PVY coat protein from a single gene and obtain the attendant resistance to PVX and PVY. Therefore, such a modified coat protein gene is considered to be within the scope of the present invention in addition to the other coat protein modifications described above.

A DNA construct of the present invention can be inserted into the genome of a plant by any suitable method. Suitable plant transformation vectors include those derived from a Ti plasmid of *Agrobacterium tumefaciens*, such as those disclosed by Herrere-Estrella (1983), Bevan (1983), Klee (1985) and EPO publication 120,516 (Schilperoort, et al.). In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, and transformation using viruses.

In one embodiment of the present invention, two double-stranded cDNA sequences, are prepared from an RNA segment (CP-mRNA) that encodes the coat protein of PVX and an RNA segment that encodes the coat protein of PVY. Coding sequences ca be individually ligated to a CaMV35S promoter, and to a suitable 3' non-translated region and subsequently combined into a singular vector, to form a DNA construct which comprises two individual plant genes. The vector is then inserted into cultured *A. tumefaciens* cells which contain a disarmed Ti plasmid. The two plasmids formed a cointegrate plasmid vector by means of a crossover event.

A DNA construct prepared in accordance with the present invention is preferably introduced, via a suitable vector as described above, into potato cells or protoplasts derived from a potato plant. Regenerated plants which are tested for virus resistance are preferably exposed to the virus at a concentration that is in a range where the rate of disease development correlates linearly with virus concentration in the inoculum. This linear range can be determined empirically, using non-transformed plants. Methods for virus inoculation are well-known to those skilled in the art, and are reviewed by Kado & Agrawal (1972). One method involves abrading a leaf surface with an aqueous suspension (typically buffered at pH 7-8) containing an abrasive material, such as carborundum or diatomaceous earth, and the virus. While inoculation in this manner is often preferred, those skilled in the art will recognize that other approaches may be used such as simply swabbing the virus inoculum on to the leaf surface or inoculation by insect vectors, such as aphids for PVY.

GENE CONSTRUCTION—PVY COAT PROTEIN (PVY—CP)

The PVY isolate used for coat protein sequencing and gene construction was a common field isolate provided by P. E. Thomas (USDA, Prosser, WA). A cDNA library was constructed in lambda gt10, coat protein gene clones were identified by probing with synthetic degenerate primers made to the deduced nucleotide sequence from N-terminal amino acid sequence determined from purified coat protein. Coat protein coding sequence clones were subcloned into M13 (New England BioLabs) and the nucleotide sequence determined. The nucleotide sequence and deduced amino acid sequence for the coat protein of PVY is shown in FIG. 1. A NcoI site was engineered in the coding sequence to provide a translational start site in front of the codon coding for the N-terminal amino acid and a BglII site engineered eleven bases upstream to provide a cloning site. The PVY engineered coat protein coding sequence and 3′ untranslated region was ligated into pMON906 vector (see FIG. 2) containing an enhanced CaMV 35S promoter (Kay, et al., 1987) and RUBISCO E9 3′ end (Coruzzi, et al., 1984) to yield intermediate vector pMON9892.

GENE CONSTRUCTION—PVX COAT PROTEIN (PVX—CP)

The coat protein gene of PVX has been definitively mapped and is located within the 3′ terminal 900 nucleotides of the genome (Morozov, et al., 1983). The nucleotide sequence and deduced amino acid sequence for the coat protein of PVX is shown in FIG. 3.

A partial PVX CP cDNA clone (p3a) that lacked the 5′ terminal 10 codons was obtained from Dr. K. G. Skryabin. This clone was synthesized by oligo(dT) priming of PVX RNA (wild strain) and cloned into the PstI site of pBR322 using dG:dC tailing (Morozov, et al., 1983). To recover the 5′ end of the CP gene, a synthetic BamHI-PstI fragment containing 18 bases of authentic 5′ non-coding sequence and 66 bases corresponding to the first 22 codons was used to replace the smaller PstI-PstI fragment containing the dG:dC tail and codons 11-22. The dG:dC tail and part of the dA:dT at the 3′ end of the gene were removed by Bal31 digestion of the larger HpaII-PstI fragment subcloned into pUC18. Then, a ClaI site was created at the 3′ end of this subclone by linker addition. Finally, the XhoI-ClaI (~170 bp) was used to replace the original 3′ end sequence from p3a and the PstI-ClaI sequence from pBR322. The final cDNA construct (in pEMBL 12+) contained 18 bp of 5′ non-coding sequence, 714 bp of PVX CP coding sequence (including TAA), 72 bp of 3′ non-coding sequence and 40 bp of dA:dT. The BamHI-ClaI fragment from this clone was inserted into BglII-ClaI sites of the expression Vector pMON 9818 (Cuozzo, et al., 1988) between the CaMV 35S promoter and the small subunit E9 3′ end to yield pMON9809 (Hemenway, et al., 1988).

TRANSFORMATION VECTOR CONSTRUCTION

An intermediate plant transformation vector pMON9898 was prepared by inserting the En35S/PVY-CP/E9 gene of pMON9892 (2.4kb HindIII fragment) into pMON9896. Plasmid pMON9896 is prepared by taking the 0.9kb EcoRV-EcoRI fragment of pMON9809 (Hemenway, et al., 1988) which contains the PVX-CP coding sequence and inserting this fragment into pMON893 (see FIG. 4). This produced plasmid pMON9896 containing an En35S/PVX-CP/7S gene. Plasmid pMON9898 therefore contains two complete genes, one which expresses PVX coat protein and the other which expresses PVY coat protein. Plasmid pMON9898 was mated into *A. tumefaciens* strain 3111SE (Rogers, et al., 1987). The modified *A. tumefaciens* carrying the co-integrate Ti plasmid (3111SE::pMON9898) was used to transform potato plants as described below. The vector carries a neomycin phosphotransferase gene which confers kanamycin resistance to transgenic plants.

TRANSFORMATION AND REGENERATION OF POTATO

Sterile shoot cultures of Russet Burbank are maintained in vials containing 10 ml of PM medium (Murashige and Skoog (MS) inorganic salts, 30 g/l surcose, 0.17 g/l Na $H_2PO_4H_2O$, o.4 mg/l thiamine-HC1, and 100 mg/l myo-inositol, solidified with 2 g/l Gelrite at pH 6.0). When shoots reached approximately 5 cm in length, stem internode segments of 7–10 mm are excised and smeared at the cut ends with *Agrobacterium tumefaciens (*3111SE::pMON9898) from a four day old plate culture. The stem explants are co-cultured for three days at 23° C. on a sterile filter paper placed over 1.5 ml of a tobacco cell feeder layer overlaid on 1/10 P medium (1/10 strength MS inorganic salts and organic addenda without casein as in Jarret, et al. (1980), 30 g/l sucrose and 8.0 g/l agar). Following co-culture the explants are transferred to full strength P-1 medium for callus induction, composed of MS inorganic salts, organic additions as in Jarret, et al. (1980) with the exception of casein, 3.0 mg/l benzyladenine (BA), and 0.01 mg/l naphthaleneacetic acid (NAA) (Jarret, et al., 1980). Carbenicillin (500 mg/l) is included to inhibit bacterial growth, and 100 mg/l kanamycin is added to select for transformed cells. After four weeks the explants are transferred to medium of the same composition but with 0.3 mg/l gibberellic acid (GA3) replacing the BA and NAA (Jarret, et al., 1981) to promote shoot formation. Shoots begin to develop approximately two weeks after transfer to shoot induction medium; these are excised and transferred to vials of P medium for rooting. Shoots are tested for kanamycin resistance conferred by the enzyme neomycin phosphotransferase II, by placing a section of the stem onto callus induction medium containing MS organic and inorganic salts, 30 g/l sucrose, 2.25 mg/l BA, 0.186 mg/l NAA, 10 mg/l GA3 (Webb, et al., 1983) and 200 mg/l kanamycin to select for transformed cells. Based on results from several experiments, approximately 10–18% of the initial explants produce shoots; of these shoots, 17–45% are transformed based on a kanamycin recallusing assay, and 30% of the transformed shoots express the PVX and PVY coat protein genes.

EXAMPLE

Russett Burbank potato cultivars were transformed and regenerated as described above using co-integrate *A. tumefaciens* vectors (3111SE:: pMON9898). Elisa and western analysis were used to detect coat protein expression from transformed potato plants. In protein extracts of transgenic plants, western analysis demonstrated expression of both PVX and PVY coat protein. Identical extracts of each transformant and untransformed Russet Burbank were run on PAGE and probed with anti-PVX IgG, anti-PVY IgG, and a mixture of both anti-PVX IgG and anti-PVY IgG.

Primary transformants were propagated by cuttings and inoculated with suspensions of PVX and/or PVY. Analysis of resistance to infection and virus spread was performed by ELISA detection of virus in extracts from inoculated and systemic leaves (see Table 1). The data of Table 1 represents plants transformed with pMON9898 (plant numbers 161, 303 and 118); plants transformed with pMON906 (vector control) and wild-type Russet Burbank Idaho (RBId) assayed by ELISA of leaf discs removed from inoculated and systemic leaves. Transgenic and wild-type Russet Burbank were propagated by cuttings into 4" plastic pots and allowed to root for fourteen days before inoculation with PVX, PVY, or PVX and PVY. Terminal leaflets of two separate leaves on each of ten plants were inoculated (using a gloved finger) with 25 μl of 2–5 μg/ml PVX, 25 μl of 5–20 μg/ml PVY or 25 μl of mixture of the two virus inoculums (one adjusted for reduced total volume). The presence of virus was determined by ELISA analysis of inoculated and systemic leaves. The analysis identified the presence of virus antigen in plant tissue. If virus was detected at all, the plant was scored as infected. The percent infected represents the number of plants out of ten plants tested which had a detectable level of virus antigen.

TABLE 1

RESISTANCE OF POTATOES TO INFECTION BY PVX AND PVY

Inoculated with PVY - Assay for PVY

| 17 Days Post Inoculation Inoculated Leaf | | 23 days Post Inoculation Inoculated Leaf | |
|---|---|---|---|
| Plant # | % Infected | Plant # | % Infected |
| 161 | 20 | 161 | 50 |
| 303 | 0 | 303 | 0 |
| 118 | 50 | 118 | 50 |
| 308(VC) | 60 | 308(VC) | 80 |
| RBId | 20 | RBId | 50 |
| Systemic Leaf | | Systemic Leaf | |
| Plant # | % Infected | Plant # | % Infected |
| 161 | 20 | 161 | 40 |
| 303 | 0 | 303 | 0 |
| 118 | 0 | 118 | 60 |
| 308(VC) | 0 | 308(VC) | 50 |
| RBId | 0 | RBId | 40 |

Inoculated with both PVY and PVX - Assay for PVY

| 17 Days Post Inoculation Inoculated Leaf | | 23 days Post Inoculation Inoculated Leaf | |
|---|---|---|---|
| Plant # | % Infected | Plant # | % Infected |
| 161 | 10 | 161 | 60 |
| 303 | 0 | 303 | 0 |
| 118 | 40 | 118 | 50 |
| 308(VC) | 40 | 308(VC) | 60 |
| RBId | 30 | RBId | 60 |
| Systemic Leaf | | Systemic Leaf | |
| Plant # | % Infected | Plant # | % Infected |
| 161 | 0 | 161 | 30 |
| 303 | 0 | 303 | 0 |
| 118 | 30 | 118 | 50 |
| 308(VC) | 10 | 308(VC) | 30 |
| RBId | 20 | RBId | 40 |

Inoculated with PVX - Assay for PVX

| 17 Days Post Inoculation Inoculated Leaf | | 23 days Post Inoculation Inoculated Leaf | |
|---|---|---|---|
| Plant # | % Infected | Plant # | % Infected |
| 161 | 10 | 161 | 10 |
| 303 | 0 | 303 | 0 |
| 118 | 10 | 118 | 10 |
| 308(VC) | 40 | 308(VC) | 50 |
| RBId | 90 | RBId | 70 |

TABLE 1-continued

RESISTANCE OF POTATOES TO INFECTION BY PVX AND PVY

| Systemic Leaf | | Systemic Leaf | |
|---|---|---|---|
| Plant # | % Infected | Plant # | % Infected |
| 161 | 0 | 161 | 10 |
| 303 | 0 | 303 | 0 |
| 118 | 0 | 118 | 0 |
| 308(VC) | 40 | 308(VC) | 50 |
| RBId | 80 | RBId | 60 |

Inoculated with both PVX and PVY - Assay for PVX

| 17 Days Post Inoculation Inoculated Leaf | | 23 days Post Inoculation Inoculated Leaf | |
|---|---|---|---|
| Plant # | % Infected | Plant # | % Infected |
| 161 | 0 | 161 | 0 |
| 303 | 0 | 303 | 0 |
| 118 | 20 | 118 | 10 |
| 308(VC) | 40 | 308(VC) | 30 |
| RBId | 50 | RBId | 50 |
| Systemic Leaf | | Systemic Leaf | |
| Plant # | % Infected | Plant # | % Infected |
| 161 | 0 | 161 | 10 |
| 303 | 0 | 303 | 0 |
| 118 | 0 | 118 | 0 |
| 308(VC) | 10 | 308(VC) | 40 |
| RBId | 30 | RBId | 60 |

Table 2 represents the data obtained from three other transformed Russet Burbank plants (204, 220 and 367). Plants were again propagated to provide a total number of ten progeny for each transformant. Inoculation levels were the same as those described for the data of Table 1. The plants were assay fourteen days post inoculation.

TABLE 2

TRANSGENIC POTATO PLANTS CHALLENGED WITH PVX AND/OR PVY

Inoculated with PVY - Assay for PVY

| Inoculated Leaf | | Systemic Leaf | |
|---|---|---|---|
| Plant # | % Infected | Plant # | % Infected |
| 367 | 80 | 367 | 30 |
| 204 | 20 | 204 | 20 |
| 220 | 60 | 220 | 40 |
| 308(VC) | 80 | 308(VC) | 70 |
| RBId | 100 | RBId | 70 |

Inoculated with PVX/PVY - Assay for PVY

| Inoculated Leaf | | Systemic Leaf | |
|---|---|---|---|
| Plant # | % Infected | Plant # | % Infected |
| 367 | 60 | 367 | 50 |
| 204 | 40 | 204 | 40 |
| 220 | 20 | 220 | 30 |
| 308(VC) | 30 | 308(VC) | 50 |
| RBId | 60 | RBId | 40 |

Inoculated with PVX/PVY - Assay for PVX

| Inoculated Leaf | | Systemic Leaf | |
|---|---|---|---|
| Plant # | % Infected | Plant # | % Infected |
| 367 | 40 | 367 | 0 |
| 204 | 10 | 204 | 0 |
| 220 | 10 | 220 | 0 |
| 308(VC) | 60 | 308(VC) | 20 |
| RBId | 80 | RBId | 30 |

Inoculated with PVX - Assay for PVX

| Inoculated Leaf | | Systemic Leaf | |
|---|---|---|---|
| Plant # | % Infected | Plant # | % Infected |
| 367 | 17 | 367 | 0 |
| 204 | 17 | 204 | 0 |
| 220 | 0 | 220 | 0 |
| 308(VC) | 33 | 308(VC) | 33 |
| RBId | 67 | RBId | 33 |

Table 3 represents the data obtained from transformed plants 204, 220 and 367 as described above for Table 2 with the exceptions that the plants were inoculated using a gauze method and assay 21 days post inoculation.

TABLE 3
TRANSGENIC POTATO PLANTS CHALLENGED WITH PVX AND/OR PVY

| Inoculated with PVY - Assay for PVY | | | |
|---|---|---|---|
| Inoculated Leaf | | Systemic Leaf | |
| Plant # | % Infected | Plant # | % Infected |
| 367 | 80 | 367 | 70 |
| 204 | 30 | 204 | 40 |
| 220 | 70 | 220 | 50 |
| 308(VC) | 80 | 308(VC) | 100 |
| RBId | 100 | RBId | 90 |
| Inoculated with PVX/PVY - Assay for PVY | | | |
| Inoculated Leaf | | Systemic Leaf | |
| Plant # | % Infected | Plant # | % Infected |
| 367 | 60 | 367 | 80 |
| 204 | 40 | 204 | 60 |
| 220 | 20 | 220 | 50 |
| 308(VC) | 60 | 308(VC) | 70 |
| RBId | 60 | RBId | 30 |
| Inoculated with PVX/PVY - Assay for PVX | | | |
| Inoculated Leaf | | Systemic Leaf | |
| Plant # | % Infected | Plant # | % Infected |
| 367 | 60 | 367 | 0 |
| 204 | 10 | 204 | 0 |
| 220 | 40 | 220 | 20 |
| 308(VC) | 60 | 308(VC) | 70 |
| RBId | 90 | RBId | 40 |
| Inoculated with PVX - Assay for PVX | | | |
| Inoculated Leaf | | Systemic Leaf | |
| Plant # | % Infected | Plant # | % Infected |
| 367 | 16.7 | 367 | 0 |
| 204 | 0 | 204 | 0 |
| 220 | 50 | 220 | 83.3 |
| 308(VC) | 33.3 | 308(VC) | 33.3 |
| RBId | 83.3 | RBId | 16.7 |

Table 4 represents the same data as described in Table 2 with the exceptions that the plants were assayed 35 days post inoculation and only systemic leaves were analyzed.

TABLE 4
TRANSGENIC POTATO PLANTS CHALLENGED WITH PVX AND/OR PVY

| Inoculated with PVY - Assay for PVY | |
|---|---|
| Plant # | % Infected |
| 367 | 100 |
| 204 | 70 |
| 220 | 70 |
| 308(VC) | 100 |
| RBId | 100 |
| Inoculated with PVX/PVY - Assay for PVY | |
| Plant # | % Infected |
| 367 | 80 |
| 204 | 70 |
| 220 | 60 |
| 308(VC) | 80 |
| RBId | 90 |
| Inoculated with PVX/PVY - Assay for PVX | |
| Plant # | % Infected |
| 367 | 0 |
| 204 | 10 |
| 220 | 0 |
| 308(VC) | 60 |
| RBId | 100 |
| Inoculated with PVX - Assay for PVX | |
| Plant # | % Infected |
| 367 | 0 |
| 204 | 0 |
| 220 | 0 |
| 308(VC) | 66 |
| RBId | 50 |

Overall, the high PVX coat protein expression levels detected in all transformants conferred a high level of resistance to PVX infection on inoculated and systemic leaves. The lower PVY coat protein expression in these transformants provided a lower level of resistance to PVY infection than that observed for PVX. One transformant #303 showed complete immunity to infection or systemic spread of both PVX and PVY. The resistance response appears to be all or none. Those transgenic plants which became infected showed control levels of virus in both inoculated and systemic leaves. The remaining plants which were not infected were essentially immune and did not show detectable virus in either inoculated or systemic leaves.

This data represents analysis of primary transformants which express different levels of viral coat protein. The level of coat protein has been correlated to the level of resistance. High challenge inoculum concentrations can overcome the engineered resistance in plants expressing low levels of coat protein. Due to variations in plant status at the time of inoculation and methods of inoculation some plants may receive more or less virus than others and this may show more or less protection against infection.

These results show genetically engineered resistance to PVY in potato by expression of PVY coat protein gene. The synergistic effect of PVY and PVX infection in potato does not appear to disturb the resistance to virus infection provided by expression of these two coat proteins in transgenic plants.

BIBLIOGRAPHY

Close, R. (1964) *Ann. Appl. Biol.* 53:151–164.
Coruzzi, G., et al. (1984) *EMBO J* 3:1671–1679.
Cuozzo, M., et al. (1988) *Bio/Technology* 6:549–557.
Damirdagh, I. S. and Ross, A. F. (1967) *Virology* 31:296–307.
Goodman, R. M. and Ross, A. F. (1974) *Virology* 58:16–24.
Hemenway, C., et al. (1988) *EMBO J* 7:1273.
Jarret, R. L., Hasegawa, P. M. and Erickson, H. T. (1980) *Physiol. Plant* 49:177.
Jarret, R. L., Hasegawa, P. M. and Bressan, R. A. (1981) *In Vitro* 17:825.
Kado, C. I. and Agrawal, H. O. (1972) *Principles and Techniques in Plant Virology.*
Kay, R., et al. (1987) *Science* 236:1299–1302.
Morozov, W. Y., Zakharyev, V. M., Cherov, B. K., Prasolov, V. S., Kozlov, Y. V., Atabekov, J. G. and Skryabin, K. G. (1983) *Dokl. Akad. Nawk. SSSR*, 271–215.
Murashige, T. and Skoog, F. (1962) *Physiol. Plant* 15:473.
Powell-Abel, P., et al. (1986) *Science* 232:738.
Rochow, W. F. and Ross, A. F. (1974) *Virology* 1:10–27.
Turner, N. E., et al. (1987) *EMBO J* 6:1181.
van Dun, C. M. P., et al. (1988) *Virology* 164:383.

Webb, K. J., Osifo, E. O. and Henshaw, G. G (1983) *Plant Sci. Letters* 30:1.

I claim:

1. A plant transformation vector which comprises a DNA molecule which encodes the coat proteins of Potato Virus X and Potato Virus Y.

2. A bacterial cell containing a plant transformation vector of claim 1.

3. A bacterial cell of claim 2 in which said bacterial cell is an *Agrobacterium tumefaciens* cell.

4. A transformed potato cell comprising heterologous DNA which encodes the coat proteins of Potato Virus X and Potato Virus Y is a chromosomal insert.

5. A transformed potato cell of claim 4 in which the cell is from a Russet Burbank potato variety.

6. A differentiated potato plant comprising transformed plant cells of claim 4 which exhibit resistance to Potato Virus X and Potato Virus Y.

7. A potato plant of claim 6 which is a Russet Burbank variety.

* * * * *